United States Patent
Hardman et al.

(10) Patent No.: US 10,978,200 B1
(45) Date of Patent: Apr. 13, 2021

(54) METHOD AND SYSTEM FOR INCREASING ACCURACY OF HYGIENE COMPLIANCE DETERMINATIONS

(71) Applicant: SWIPESENSE, INC., Chicago, IL (US)

(72) Inventors: Jori Hardman, Chicago, IL (US); Harikrishna K. Rajabather, Dallas, TX (US); Won Il Kim, Jersey City, NJ (US); Nathan Lloyd Ward, Brooklyn, NY (US); Yuri F. Malina, Chicago, IL (US)

(73) Assignee: SwipeSense, Inc., Chicago, IL (US)

( * ) Notice: Subject to any disclaimer, the term of this patent is extended or adjusted under 35 U.S.C. 154(b) by 0 days.

(21) Appl. No.: 16/540,903

(22) Filed: Aug. 14, 2019

Related U.S. Application Data (63) Continuation of application No. 16/116,374, filed on Aug. 29, 2018.

(60) Provisional application No. 62/552,056, filed on Aug. 30, 2017.

(51) Int. Cl.
| | |
|---|---|
| G06F 15/16 | (2006.01) |
| G16H 40/20 | (2018.01) |
| H04L 29/08 | (2006.01) |
| G06K 7/10 | (2006.01) |

(52) U.S. Cl.
CPC ............ G16H 40/20 (2018.01); H04L 67/12 (2013.01); G06K 7/10425 (2013.01)

(58) Field of Classification Search
CPC ..... G16H 40/20; H04L 67/12; G06K 7/10425
See application file for complete search history.

(56) References Cited

U.S. PATENT DOCUMENTS

| | | | |
|---|---|---|---|
| 6,459,989 B1 | 10/2002 | Kirkpatrick et al. | |
| 7,257,411 B2 | 8/2007 | Gwon et al. | |
| 10,013,831 B1* | 7/2018 | Kusens | ............... H04W 64/00 |
| 2003/0146835 A1* | 8/2003 | Carter | .................. G01S 5/0252 |
| | | | 340/539.13 |
| 2004/0248589 A1 | 12/2004 | Gwon et al. | |
| 2008/0191941 A1 | 8/2008 | Saban et al. | |
| 2010/0039929 A1 | 2/2010 | Cho et al. | |
| 2010/0109842 A1 | 5/2010 | Patel et al. | |
| 2010/0117836 A1 | 5/2010 | Momen et al. | |
| 2010/0315244 A1 | 12/2010 | Tokhtuev et al. | |
| 2010/0321180 A1 | 12/2010 | Dempsey et al. | |
| 2010/0328443 A1 | 12/2010 | Lynam et al. | |
| 2011/0227740 A1 | 9/2011 | Wohltjen | |
| 2012/0072110 A1 | 3/2012 | Venkatraman | |
| 2012/0203453 A1 | 8/2012 | Lundquist et al. | |

(Continued)

FOREIGN PATENT DOCUMENTS

WO    2009097096 A1    8/2009

*Primary Examiner* — Jonathan A Bui
(74) *Attorney, Agent, or Firm* — Renaissance IP Law Group, LLP; David A. Crowther (57) ABSTRACT

Embodiments of the present inventive concept leverage RSS patterns, accelerometer patterns, hygiene event information, and hub locations to increase accuracy of room-level positioning of objects and people, and to ensure a high accuracy detection of zone entry and/or exit times in an indoor environment, all of which facilitate an accurate hand hygiene compliance monitoring system in hospitals and other medical facilities, as well as a variety of other applications.

17 Claims, 6 Drawing Sheets

(56) References Cited

U.S. PATENT DOCUMENTS

| | | | |
|---|---|---|---|
| 2012/0264447 A1* | 10/2012 | Rieger, III | H04W 4/025 |
| | | | 455/456.1 |
| 2014/0148196 A1 | 5/2014 | Bassan-Eskenazi et al. | |
| 2014/0222521 A1 | 8/2014 | Chait | |
| 2015/0310180 A1* | 10/2015 | Pattekar | G16H 40/20 |
| | | | 705/2 |
| 2016/0026837 A1* | 1/2016 | Good | G01S 5/0289 |
| | | | 340/539.13 |
| 2016/0125348 A1* | 5/2016 | Dyer | H04W 4/33 |
| | | | 705/7.42 |
| 2016/0247342 A1* | 8/2016 | Kusens | G07C 9/00817 |
| 2016/0267772 A1* | 9/2016 | Iseri | G16H 40/20 |
| 2016/0323754 A1* | 11/2016 | Friday | H04W 16/28 |
| 2017/0013409 A1* | 1/2017 | Cerchio | H04W 72/0473 |
| 2017/0041452 A1* | 2/2017 | Amann | H04B 17/23 |
| 2017/0365157 A1* | 12/2017 | Shoari | B65C 9/40 |
| 2018/0160269 A1* | 6/2018 | Baarman | G06Q 50/12 |
| 2019/0043337 A1* | 2/2019 | Liu | G16H 40/20 |
| 2019/0080796 A1* | 3/2019 | Greiner | G16H 40/20 |
| 2019/0117809 A1* | 4/2019 | Katz | G06K 9/00201 |
| 2019/0213860 A1* | 7/2019 | Shaprio | H02J 7/025 |
| 2019/0311800 A1* | 10/2019 | Patel | G16H 40/40 |
| 2019/0342697 A1* | 11/2019 | Morgan | H04W 16/24 |

* cited by examiner

METHOD AND SYSTEM FOR INCREASING ACCURACY OF HYGIENE COMPLIANCE DETERMINATIONS

RELATED APPLICATION DATA

This application is a continuation of U.S. application Ser. No. 16/116,374, filed on Aug. 29, 2018, which claims the benefit of U.S. Provisional Patent Application Ser. No. 62/552,056, filed on Aug. 30, 2017, which are hereby incorporated by reference.

TECHNICAL FIELD

This application pertains to hand hygiene, and more particularly, to a method and system for increasing accuracy of hygiene compliance in medical facilities.

BACKGROUND

Each year in the U.S. there are hundreds of thousands of hospital-acquired infections caused by poor hand hygiene. Current electronic hand hygiene monitoring systems suffer from low accuracy. For example, conventional systems fail to correctly determine when a staff member was required to sanitize their hands, and may also fail to correctly determine when a staff member sanitizes their hands. Wireless sensor networks have been deployed to assist in making these determinations. One of the primary problems with conventional systems is that the received signal strength (RSS) in wireless sensor networks present significant challenges for position tracking in indoor environments.

For example, current systems use singular approaches to determining when a staff member was required to sanitize their hands. Various existing systems have settled on a specific wavelength of radio waves for communication and specific methods for using these communication characteristics to determine the location of medical staff. However, each has specific drawbacks leading to significant challenges in producing a highly accurate (e.g., 90%) zone detection system to accurately determine when a user is required to sanitize their hands and accurately monitor hand hygiene compliance.

Various conventional approaches have been implemented to determine whether medical staff are inside of a predetermined zone in an indoor environment. However, distance and position estimation in indoor environments suffer from low accuracy due to multi-path effects, attenuation from walls, equipment, furniture, and the human body, which lead to incorrect estimations about whether medical staff are in the correct zones at the correct times. In the case where a radio frequency (RF) wavelength is selected that requires line of sight such as infrared, low accuracy is often the result due to frequently interrupted line of sight, and signal reflections between the location beacon and the tag.

Accordingly, a need remains for an improved method and system for increasing accuracy of hygiene compliance. Embodiments of the inventive concept address these and other limitations in the prior art.

The foregoing and other features of the inventive concept will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first sensor could be termed a second sensor, and, similarly, a second sensor could be termed a first sensor, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the present inventive concept leverage RSS patterns, accelerometer patterns, hygiene event information, and hub locations to increase accuracy of room-level positioning of objects and people, and to ensure a high accuracy detection of zone entry and/or exit times in an indoor environment, all of which facilitate an accurate hand hygiene compliance monitoring system in hospitals and medical facilities, as well as a variety of other applications.

Figure 1A:
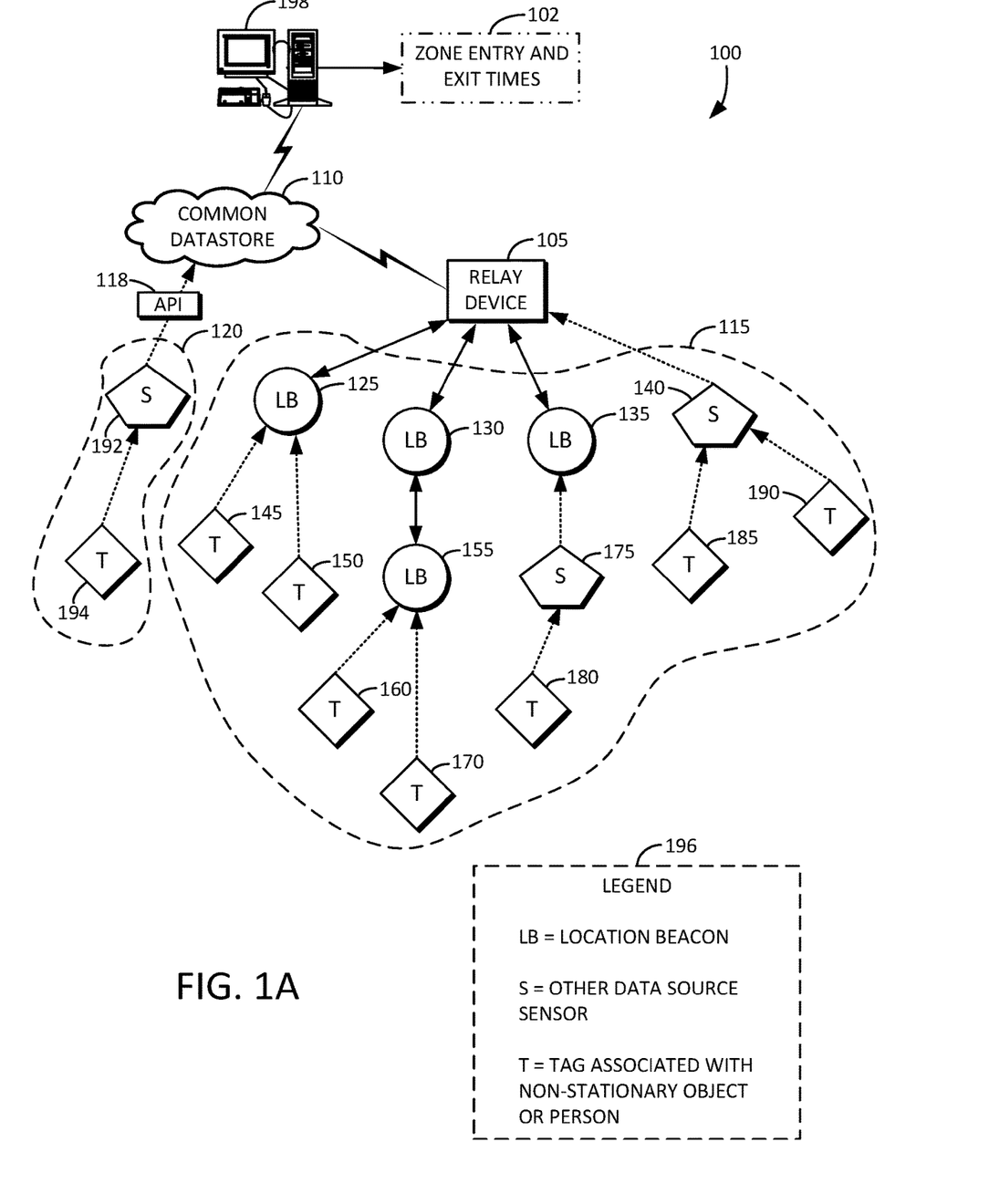
FIG. 1A illustrates a schematic diagram of an example system for increasing the accuracy of hygiene compliance determinations in accordance with various embodiments of the present inventive concept.
Figure 1B:
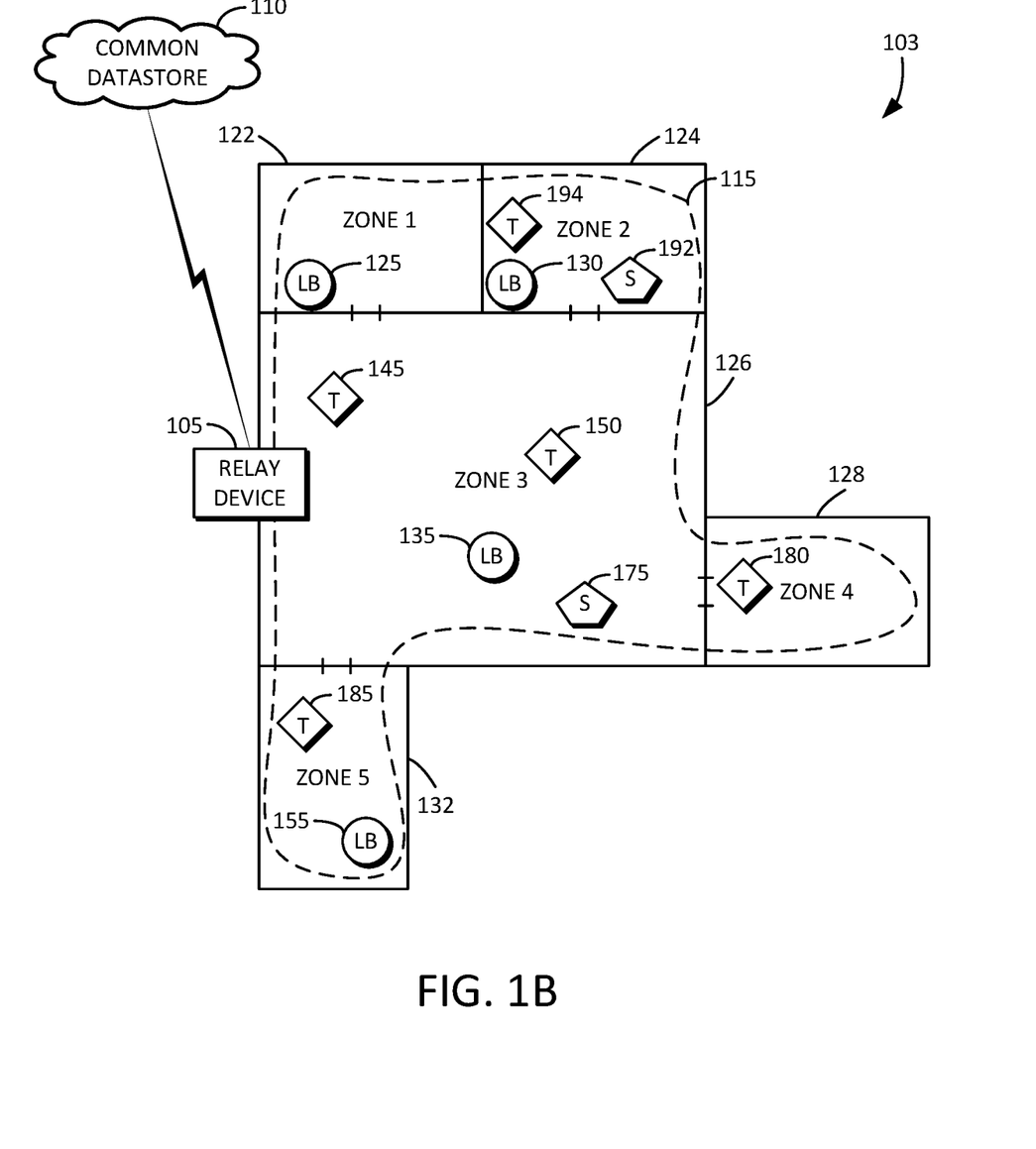
FIG. 1B illustrates a schematic diagram of an example medical facility with various zones in accordance with various embodiments of the present inventive concept.
Figure 1C:
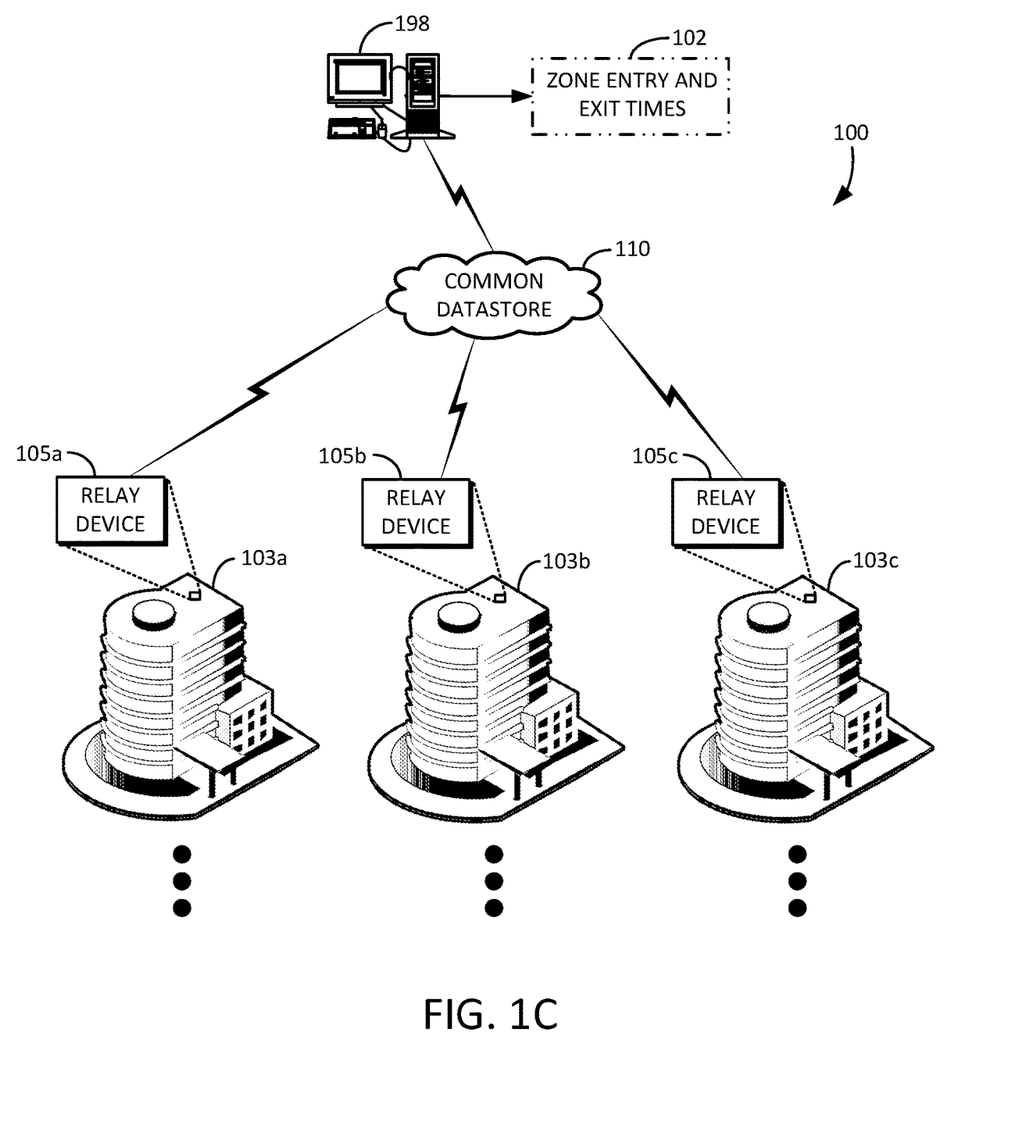
FIG. 1C illustrates a schematic diagram of an example system for increasing the accuracy of hygiene compliance determinations across multiple medical facilities in accordance with various embodiments of the present inventive concept.
Figure 2:
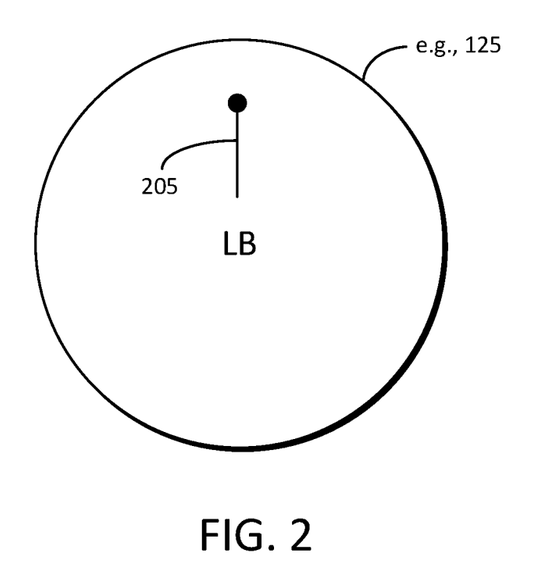
FIG. 2 illustrates a schematic diagram of an example location beacon of FIG. 1A.
Figure 3:
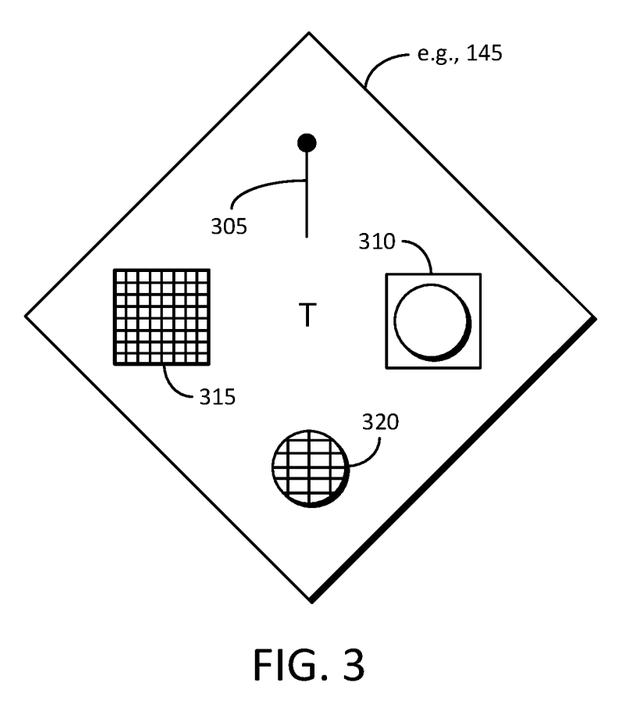
FIG. 3 illustrates a schematic diagram of an example tag of FIG. 1A.
Figure 4:
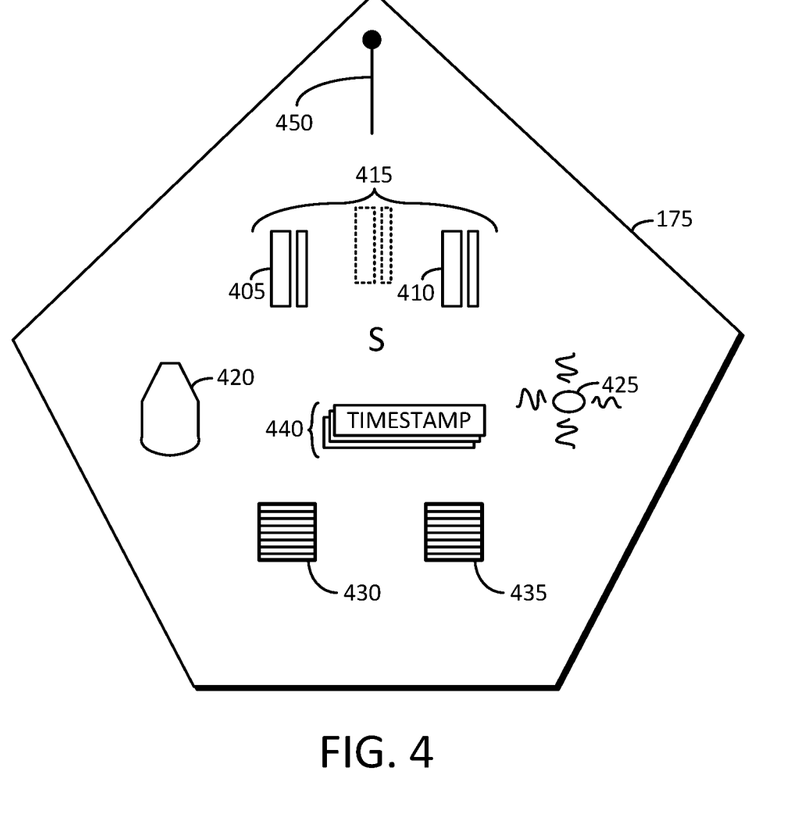
FIG. 4 illustrates a schematic diagram of an example hygiene compliance data source sensor of FIG. 1A.

FIG. 1A illustrates a schematic diagram of an example system 100 for increasing the accuracy of hygiene compliance in accordance with various embodiments of the present inventive concept. FIG. 1B illustrates a schematic diagram of an example medical facility 103 with various zones in accordance with various embodiments of the present inventive concept. FIG. 1C illustrates a schematic diagram of the example system 100 for increasing the accuracy of hygiene compliance determinations across multiple medical facilities in accordance with various embodiments of the present inventive concept. FIG. 2 illustrates a schematic diagram of an example location beacon (e.g., 125) of FIG. 1A. FIG. 3 illustrates a schematic diagram of an example tag (e.g., 145) of FIG. 1A. FIG. 4 illustrates a schematic diagram of an example hygiene compliance data source sensor (e.g., 175) of FIG. 1A. Reference is now made to FIGS. 1A through 4.

A legend 196 is provided, which includes the meaning of "LB" (location beacon), "S" (other hygiene compliance data source sensor), and T (tag associated with a non-stationary object or person). Location beacons (e.g., LB 125, LB 130, LB 135, and LB 155) can be placed in known locations. Each of the location beacons can be equipped with a radio transceiver 205, as shown in FIG. 2. Tags (e.g., T 145, T 150, T 155, T 160, T 170, T 180, T 185, T 190, and T 194) can be placed on any non-stationary object or person (e.g., staff, equipment, supplies, or the like). The tags may have an unknown location, at least initially. Each of the tags can be equipped with a radio transceiver 305, as shown in FIG. 3. In some embodiments, each of the tags can be equipped with a radio transmitter rather than a transceiver. Each of the tags can also include a motion detector 310 such as an accelerometer, a gyroscope, a magnetometer, or the like. The motion detector 310 can detect motion of the of the tags. Each of the tags (e.g., T 145, T 150, T 155, T 160, T 170, T 180, T 185, T 190, and T 194) can transmit a subset of the hygiene compliance data including motion detection data to the location beacons (e.g., LB 125, LB 130, LB 135, and LB 155). The location beacons can transmit the subset of the hygiene compliance data including the motion detection data to a common hygiene compliance datastore 110.

Moreover, each of the tags can include an ultrasound speaker 315 and/or ultrasound microphone 320. The tags (e.g., T 145, T 150, T 155, T 160, T 170, T 180, T 185, T 190, and T 194) can transmit a subset of the hygiene compliance data including ultrasound data to the location beacons (e.g., LB 125, LB 130, LB 135, and LB 155), which can transmit the subset of the hygiene compliance data including the ultrasound data to the common hygiene compliance datastore 110.

The system 100 can include other hygiene compliance data source sensors (e.g., S 140, S 175, and S 192). In some embodiments, the other hygiene compliance data source sensors can include a door entry detector 405 and/or door exit detector 410, as shown in FIG. 4. In some embodiments the door entry detector 405 and the door exit detector 410 comprise a single door entry and exit detector 415. The door entry and exit detector 415 can detect when a person enters or exits a particular room in the medical facility 103. In some embodiments, the other hygiene compliance data source sensors can include a hygiene dispenser detector 420, a presence detector 425, one or more workstation logs 430, one or more timestamps 440, one or more schedules 435, or the like. The presence detector 425, for example, can detect a presence of a person in a particular area or zone of the medical facility 103. The schedules 435 can include information about the work schedules, for example, of persons who work at the medical facility 103. When determining which person is responsible for using a particular hygiene dispenser, it is more likely to be the particular person if the dispenser usage occurs during the person's regular work schedule. Similarly, the workstation logs 430 can be used to check whether a particular person was in the same room performing work on a particular workstation when a particular hygiene dispenser was used, thereby increasing the accuracy of the assessment of who used the particular hygiene dispenser at a given time. The hygiene compliance data source sensors (e.g., S 140, S 175, and S 192) can each include a transceiver 450 for transmitting gathered hygiene compliance data to the relay device 105 or directly to the common datastore 110 using the API 118.

The location beacons, the tags, and the other hygiene compliance data source sensors can all be configured to transmit their raw or processed data to the common data store 110. The transmitted data can be submitted to the data store 110 directly or through one or more relays 105. The data store 110 can be housed in a central or remote computer server 198. The data store 110 can exist in the cloud.

In some embodiments, the system 100 relays multiple sources of compliance data, such as from location beacons, tags, and other hygiene compliance data source sensors, to a single hygiene compliance datastore 110. The sources of data can include, for example, (i) received signal strength data between a tag (e.g., 145) and one or more location beacons (e.g., 125), collected at one or more radio frequencies, (ii) time-of-flight data between the tag (e.g., 145) and one or more location beacons (e.g., 125), (iii) tag accelerometer, orientation, heading, or other tag movement data, (iv) known positions of location beacons (e.g., 125) in a common coordinate system, (v) tag movement paths in a common coordinate system, encoding possible and impossible transitions from one location to another, (vi) data from other hygiene compliance sensors or devices (e.g., S 140) besides tags and location beacons such as: usage logs 430 of workstations in known locations, one or more timestamps 440 associated with a given tag (e.g., 145), for example, from a door entry detector 405 and/or exit detector 410, or (v) timestamps 440 associated with a given tag (e.g., 145) related to a hygiene dispenser detector 420 that detects use of a hygiene dispenser. The system 100 is configured to process data from at least two data sources (e.g., location beacons, tags, or other hygiene compliance data source sensors) contained in the data store 110, and then output zone entry times and zone exit times 102. The zone entry and exit times can correlate, for example, to the entry or exit of zones (e.g., 122, 124, 126, 128, and 132) of the medical facility 103, as illustrated in FIG. 1B. In other words, the system 101 can keep track of transits of humans from one zone to another zone within the medical facility 103. The medical facility 103 can be a hospital, a clinic, an urgent care facility, or other type of healthcare facility. The zones (e.g., 122, 124, 126, 128, and 132) need not correlate with specific rooms. Rather, one zone can include two or more rooms. Conversely, one room can include two or more zones. The zone entry and exit times 102 can be used in combination with other data such as dispenser usage to place object or people in certain spaces and at certain times, which increases the accuracy of identifying those people who are behaving in a compliant manner with respect to hand hygiene.

The system 100 can use data from one location beacon (e.g., LB 125, LB 130, LB 135, and LB 155) and data from one tag (e.g., T 145, T 150, T 155, T 160, T 170, T 180, T 185, T 190, and T 194). By way of another example, the system 100 can use data from one location beacon (e.g., LB 125, LB 130, LB 135, and LB 155) and data from one other data source sensor (e.g., S 140, S 175, and S 192). By way of still another example, the system 100 can use data from one tag (e.g., T 145, T 150, T 155, T 160, T 170, T 180, T 185, T 190, and T 194) and data from one other data source sensor (e.g., S 140, S 175, and S 192). By way of yet another example, the system 100 can use data from a location beacon, a tag, and a data source sensor. The system can generate and output the zone entry times and zone exit times 102 based on the gathered and processed data. The location beacons (e.g., LB 125, LB 130, LB 135, and LB 155) can be situated in the various zones (e.g., 122, 124, 126, 128, and 132).

Some or all data sources can be connected to the common data store 110 directly through an application programming interface (API) 118, as shown at 120, or other data exchange method. In some embodiments, location beacons and data sources can form a mesh network 115 in a medical facility 103, and route data to one or more relays (e.g., 105) that post data to the common hygiene compliance datastore 110 through the API 118.

Due to the large variation in indoor environments, building construction, types of objects to be tracked, and the fact that these environments also vary with time, any single data source is insufficient to accurately (e.g., >90%) determine zone entry and exit times 102 of non-stationary objects and persons. The system 100 allows for various data sources to be collected, combined and weighted, which results in a more accurate tracking compared to the use of a single data source. For example, information provided by the tags (e.g., T 145, T 150, T 155, T 160, T 170, T 180, T 185, T 190, and T 194) can be given a higher weight than information provided by other hygiene compliance data source sensors (e.g., S 140, S 175, and S 192) when determining the zone entry times and zone exit times 102, or vice versa. The types of data sources that can be collected in a single data store 110 can be expanded to include other sensors such as presence detectors, appointment scheduling systems, or the like. The system 100 can be used to determine compliance of hospital staff with hand hygiene guidelines. Due to rules and regulations, staff are supposed to perform hand hygiene upon entering and exiting pre-determined zones, but often times do not comply. The system 100 therefore increases hygiene compliance by determining location of medical staff including transits from one zone to another within the medical facility 103 so as to prove presence. The proof of presence can then be used to determine whether a particular medical staff employee was actually the person who used a hygiene dispenser within a particular zone. The system can track objects as well as people. The combination of zone entry and exit times 102 with hand hygiene dispenser usage data can increase the accuracy of hand hygiene dispenser usage rates.

As shown in FIG. 1B, the medical facility 103 can have multiple rooms (e.g., 122, 124, 126, 128, and 132). In some embodiments, various zones (e.g., Zone 1, Zone 2, Zone 3, Zone 4, and Zone 5) of the medical facility 103 correspond to the various rooms (e.g., 122, 124, 126, 128, and 132). It will be understood that this need not necessarily be the case. In other words, in some embodiments, a particular zone could encompass two or more rooms, or a particular room could encompass two or more zones. The example diagram in FIG. 1B. shows the location beacon 125 situated within the Zone 1 and the room 122. The location beacon 130 is situated within the Zone 2 and the room 124. The location beacon 135 is situated within the Zone 3 and the room 126. The location beacon 155 is situated within the Zone 5 and the room 132.

Various tags (e.g., T 194, T 145, T 180, and T 185) are mobile and are shown at various places within the medical facility 103, such as in Zones 2, 3, 4, and 5 and rooms 124, 126, 128, and 132. The tags can transit through the various zones based on the movement of the objects or people to which the tags are attached. In addition, the hygiene compliance data source sensor S 175 is situated within the Zone 3 and the room 126. The hygiene compliance data source sensor S 192 is situated within the Zone 2 and the room 124. Some or all of the location beacons, the tags, and the hygiene compliance data source sensor may be communicatively coupled using the mesh network 115. The relay device 105 can be located in or associated with the medical facility 103. The relay device 105 can relay gathered data from the location beacons, tags, and/or hygiene compliance data source sensors to the common hygiene compliance datastore 110, which can then be processed to determine the entry and exit times 102, which can be used to increase the accuracy of hygiene compliance determinations.

As shown in FIG. 1C, multiple relay devices (e.g., 105a, 105b, 105c, etc.) can be situated in multiple medical facilities (e.g., 103a, 103b, 103c, etc.). Each of the relay devices (e.g., 105a, 105b, 105c, etc.) can be communicatively coupled to the common datastore 110. The common datastore 110 can store hygiene compliance information across all of the medical facilities (e.g., 103a, 103b, 103c, etc.). The remote computer server 198 can access the hygiene compliance information for all of the medical facilities (e.g., 103a, 103b, 103c, etc.) by accessing the common datastore 110. The remote computer server 198 can generate the zone entry and exit times 102 for any one or more of the medical facilities (e.g., 103a, 103b, 103c, etc.).

Figure 5:
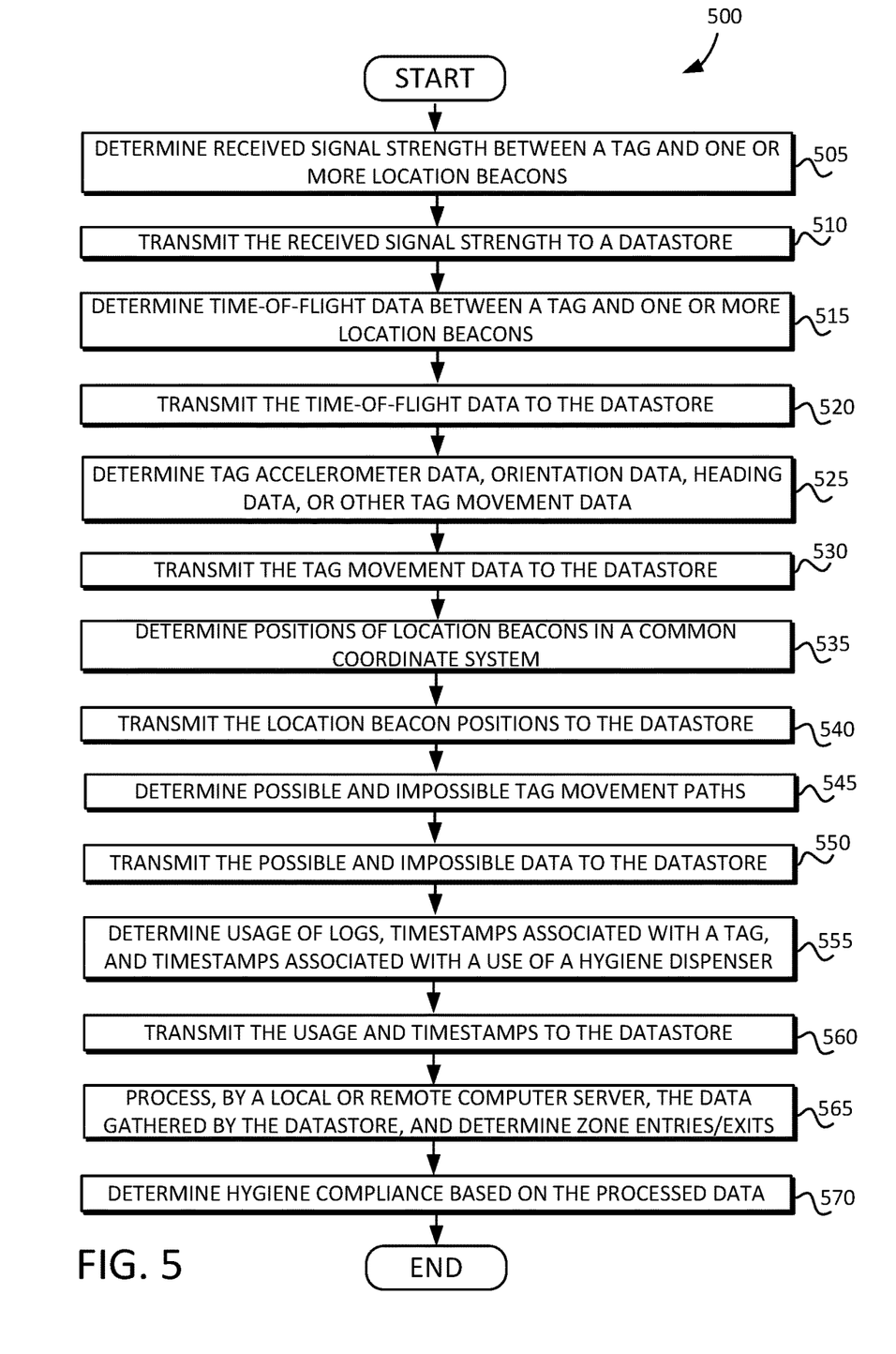
FIG. 5 is a flow diagram illustrating an example technique for improving the accuracy of hygiene compliance determinations in accordance with various embodiments of the present inventive concept.

FIG. 5 is a flow diagram 500 illustrating an example technique for improving the accuracy of hygiene compliance determinations in accordance with various embodiments of the present inventive concept. It will be understood that the steps need not be performed in the order shown, and intervening steps may be present. At 505, a received signal strength can be determined between a tag and one or more location beacons. At 510, the received signal strength can be transmitted to a common hygiene compliance datastore via a mesh network. At 515, a time-of-flight data can be determined between a tag and one or more location beacons. In other words, the time that a tag leaves the ambit of a particular location beacon can be determined and recorded. At 520, the time-of-flight data can be transmitted to the common hygiene compliance datastore via the mesh network. At 525, tag accelerometer data, orientation data, heading data, or other tag movement data can be determined. At 530, the tag movement data can be transmitted to the common hygiene compliance datastore via the mesh network. At 535, positions of location beacons in a common coordinate system can be determined. At 540, the location beacon positions can be transmitted to the common hygiene compliance datastore via the mesh network. At 545, possible and impossible tag movement paths can be determined. At 550, the possible and impossible tag movement path data can be transmitted to the common hygiene compliance datastore via the mesh network. At 555, usage of logs, timestamps associated with a tag, and/or timestamps associated with a use of a hygiene dispenser can be determined. At 560, the usage and timestamp data can be transmitted to the common hygiene compliance datastore via the mesh network. At 565, a local or remote computer server can process the data gathered by the common hygiene compliance datastore, and determine zone entry and exit times. At 570, the local or remote computer server can determine hygiene compliance based on the processed data.

The system 100 and method described herein can be applied more broadly to any situation where a non-stationary object's presence and transition between predetermined zones must be tracked accurately, such as in: inventory management, food services, workflow management, manufacturing, or process control.

Embodiment of the present inventive concept include a system for increasing accuracy of hygiene compliance in medical facilities. The system can include a remote computer server. The system can include a relay device situated within a medical facility and configured to relay hygiene compliance data to a common hygiene compliance datastore, wherein the remote computer server is communicatively coupled to the common hygiene compliance datastore and configured to receive the hygiene compliance data from the common hygiene compliance datastore. The system can include one or more location beacons situated in a corresponding one or more known locations within a plurality of zones of the medical facility, wherein the one or more location beacons include a transceiver, wherein the one or more location beacons are communicatively coupled to the relay device, and configured to transmit a first subset of the hygiene compliance data to the relay device. The system can include a plurality of tags having an initial unknown location, each of the tags including one or more of a transceiver or a transmitter, each of the tags being attached to one or more of a non-stationary object or a non-stationary person, wherein the one or more location beacons are configured to detect a signal strength between the plurality of tags and the one or more location beacons, wherein the one or more location beacons are configured to transmit, via the transceiver of the one or more location beacons, the signal strength to the relay device, and wherein the first subset of the hygiene compliance data includes the signal strength between the plurality of tags and the one or more location beacons. In some embodiments, the remote computer server is configured to generate zone entry and exit times of the tags transiting the plurality of zones based at least on the first subset of the hygiene compliance data that is stored in the common hygiene compliance datastore.

In some embodiments, the system can include a hygiene compliance data source sensor communicatively coupled directly to the common hygiene compliance datastore via an application programming interface (API), wherein the hygiene compliance data source sensor is configured to transmit a second subset of the hygiene compliance data to the common hygiene compliance datastore.

In some embodiments, the remote computer server is configured to generate the zone entry and exit times of the tags transiting the plurality of zones based at least on the first subset of the hygiene compliance data and the second subset of the hygiene compliance data that is stored in the common hygiene compliance datastore.

In some embodiments, each of the plurality of tags include a motion detector to detect motion of the plurality of tags, wherein each of the plurality of tags is configured to transmit a third subset of the hygiene compliance data including motion detection data to the one or more location beacons, wherein the one or more location beacons are configured to transmit the third subset of the hygiene compliance data to the common hygiene compliance datastore.

In some embodiments, the motion detector includes one or more of an accelerometer, a gyroscope, or a magnetometer.

In some embodiments, the remote computer server is configured to generate the zone entry and exit times of the tags transiting the plurality of zones based at least on the first subset of the hygiene compliance data, the second subset of the hygiene compliance data, and the third subset of the hygiene compliance data.

In some embodiments, each of the plurality of tags include one or more of an ultrasound speaker or an ultrasound microphone, wherein each of the plurality of tags is configured to transmit a fourth subset of the hygiene compliance data including ultrasound data to the one or more location beacons, wherein the one or more location beacons are configured to transmit the fourth subset of the hygiene compliance data to the common hygiene compliance datastore.

In some embodiments, the hygiene compliance data source sensor includes a door entry and exit detector configured to detect when the non-stationary person enters or exits a particular room of the medical facility.

In some embodiments, the hygiene compliance data source sensor includes a hygiene dispenser detector configured to detect use by the person of a hygiene dispenser.

In some embodiments, the hygiene compliance data source sensor includes a presence detector configured to detect a presence of the person in a particular zone from among the plurality of zones of the medical facility.

In some embodiments, the hygiene compliance data source sensor includes one or more timestamps associated with a given tag from among the plurality of tags.

In some embodiments, the hygiene compliance data source sensor includes one or more of a transceiver or a transmitter, a door entry and exit detector configured to detect when the non-stationary person enters or exits a particular room of the medical facility, a hygiene dispenser detector configured to detect use by the person of a hygiene dispenser, a presence detector configured to detect a presence of the person in a particular zone from among the plurality of zones of the medical facility, and one or more timestamps associated with a given tag from among the plurality of tags.

In some embodiments, the hygiene compliance data source sensor is configured to transmit, via the one or more of the transceiver or the transmitter, a fifth subset of the hygiene compliance data including door entry and exit data, hygiene dispenser usage data, presence data, and the one or more timestamps, to the one or more location beacons, wherein the one or more location beacons are configured to transmit the fifth subset of the hygiene compliance data to the common hygiene compliance datastore.

In some embodiments, the remote computer server is configured to generate the zone entry and exit times of the tags transiting the plurality of zones based at least on the first subset of the hygiene compliance data, the second subset of the hygiene compliance data, and the fifth subset of the hygiene compliance data.

The system can further include a plurality of relay devices each situated within a corresponding plurality of medical facilities. In some embodiments, each of the relay devices is configured to relay hygiene compliance data from each of the plurality of medical facilities to the common hygiene compliance datastore. In some embodiments, the remote computer server is configured to receive the hygiene compliance data associated with the plurality of medical facilities from the common hygiene compliance datastore.

Embodiments of the inventive concept include a computer implemented method for increasing accuracy of hygiene compliance in medical facilities. The method can include determining received signal strength between a tag and one or more location beacons. The method can include transmitting the received signal strength to a common hygiene compliance datastore. The method can include determining time-of-flight data between the tag and the one or more location beacons. The method can include transmitting the time-of-flight data to the common hygiene compliance datastore. The method can include determining one or more of tag accelerometer data, orientation data, heading data, or tag movement data. The method can include transmitting the one or more of the tag accelerometer data, the orientation data, the heading data, or the tag movement data to the common hygiene compliance datastore. The method can include processing, by a computer, data stored in the common hygiene compliance datastore. The method can include determining hygiene compliance based at least on the processed data. The method can include determining positions of a plurality of location beacons in a common coordinate system. The method can include transmitting the positions of the plurality of location beacons to the common hygiene compliance datastore. The method can include determining possible and impossible movement paths of the tag. The method can include transmitting the possible and impossible movement paths of the tag to the common hygiene compliance datastore. The method can include determining one or more of usage of logs, timestamps associated with the tag, or timestamps associated with a use of a hygiene dispenser. The method can include transmitting the one or more of the usage of logs, the timestamps associated with the tag, or the timestamps associated with the use of a hygiene dispenser to the common hygiene compliance datastore. The method can include processing, by the computer, the data stored in the common hygiene compliance datastore. The method can include determining the hygiene compliance based at least on the processed data.

Embodiments are described herein, and illustrated in the drawings, in terms of functional blocks, units and/or modules. Those skilled in the art will appreciate that these blocks, units and/or modules can be physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

The following discussion is intended to provide a brief, general description of a suitable machine or machines in which certain aspects of the inventive concept can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long-range carriers and protocols, including radio frequency (RF), satellite, microwave, Institute of Electrical and Electronics Engineers (IEEE) 545.11, Bluetooth®, optical, infrared, cable, laser, etc.

Embodiments of the inventive concept can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the inventive concept with reference to illustrated embodiments, it will be recognized that the illustrated embodiments can be modified in arrangement and detail without departing from such principles, and can be combined in any desired manner And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the inventive concept to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the embodiments as described herein.

Consequently, in view of the wide variety of permutations to the embodiments described herein, this detailed description and accompanying material is intended to be illustrative only, and should not be taken as limiting the scope of the inventive concept. What is claimed as the invention, therefore, is all such modifications as may come within the scope and spirit of the following claims and equivalents thereto.

The invention claimed is:

1. A system for increasing accuracy of location tracking in medical facilities, the system comprising:
   a remote computer server;
   a relay device situated within a medical facility and configured to relay location data to a datastore, wherein the remote computer server is communicatively coupled to the datastore and configured to receive the location data from the datastore;
   one or more location beacons situated in a corresponding one or more known locations within a plurality of zones of the medical facility, wherein the one or more location beacons include a transceiver, wherein the one or more location beacons are communicatively coupled to the relay device, and configured to transmit the location data to the relay device;
   a plurality of tags having an initial unknown location, each of the tags including one or more of a transceiver or a transmitter, each of the tags being attached to one or more of a non-stationary object or a non-stationary person, wherein the one or more location beacons are configured to detect a signal strength between the plurality of tags and the one or more location beacons, and wherein a first subset of the location data includes the signal strength between the plurality of tags and the one or more location beacons; and
   wherein the remote computer server is configured to generate zone entry and exit times of the tags transiting the plurality of zones based at least on the first subset of the location data that is stored in the datastore.

2. The system for increasing accuracy of location tracking of claim 1, wherein the remote computer server is configured to generate the zone entry and exit times of the tags transiting the plurality of zones based at least on the first subset of the location data that is stored in the datastore.

3. The system for increasing accuracy of location tracking of claim 1, wherein each of the plurality of tags include a motion detector to detect motion of the plurality of tags, wherein each of the plurality of tags is configured to transmit a second subset of the location data including motion detection data to the one or more location beacons, wherein the one or more location beacons are configured to transmit the second subset of the location data to the datastore.

4. The system for increasing accuracy of location tracking of claim 3, wherein the motion detector includes one or more of an accelerometer, a gyroscope, or a magnetometer.

5. The system for increasing accuracy of location tracking of claim 3, wherein the remote computer server is configured to generate the zone entry and exit times of the tags transiting the plurality of zones based at least on the first subset of the location data and the second subset of the location data.

6. The system for increasing accuracy of location tracking of claim 3, wherein each of the plurality of tags include one or more of an ultrasound speaker or an ultrasound microphone, wherein each of the plurality of tags is configured to transmit a third subset of the location data including ultrasound data to the one or more location beacons, wherein the one or more location beacons are configured to transmit the third subset of the location data to the datastore.

7. The system for increasing accuracy of location tracking of claim 6, further comprising a data source sensor including a door entry and exit detector configured to detect when the one or more of the non-stationary object or the non-stationary person enters or exits a particular room of the medical facility.

8. The system for increasing accuracy of location tracking of claim 7, wherein the data source sensor is a first data source sensor, the system further comprising a second data source sensor including a presence detector configured to detect a presence of the one or more of the non-stationary object or the non-stationary person in a particular zone from among the plurality of zones of the medical facility.

9. The system for increasing accuracy of location tracking of claim 7, wherein the data source sensor includes one or more timestamps associated with a given tag from among the plurality of tags.

10. The system for increasing accuracy of location tracking of claim 7, wherein the data source sensor includes:
    one or more of a transceiver or a transmitter;
    a door entry and exit detector configured to detect when the one or more of the non-stationary object or the non-stationary person enters or exits a particular room of the medical facility;
    a presence detector configured to detect a presence of the one or more of the non-stationary object or the non-stationary person in a particular zone from among the plurality of zones of the medical facility; and
    one or more timestamps associated with a given tag from among the plurality of tags.

11. The system for increasing accuracy of location tracking of claim 10, wherein:
    the data source sensor is configured to transmit, via the one or more of the transceiver or the transmitter, a fourth subset of the location data including door entry and exit data, presence data, and the one or more timestamps, to the one or more location beacons, wherein the one or more location beacons are configured to transmit the fourth subset of the location data to the datastore.

12. The system for increasing accuracy of location tracking of claim 11, wherein the remote computer server is configured to generate the zone entry and exit times of the tags transiting the plurality of zones based at least on the first subset of the location data, the second subset of the location data, the third subset of the location data, and the fourth subset of the location data.

13. The system for increasing accuracy of location tracking of claim 1, further comprising:
    a plurality of relay devices each situated within a corresponding plurality of medical facilities;
    wherein each of the relay devices is configured to relay the location data from each of the plurality of medical facilities to the datastore, wherein the remote computer server is configured to receive the location data associated with the plurality of medical facilities from the datastore.

14. A computer implemented method for increasing accuracy of location tracking in medical facilities, the method comprising:
- determining, by one or more location beacons, received signal strength between a tag and the one or more location beacons, wherein the tag is associated with an object;
- transmitting and storing the received signal strength to a datastore;
- determining one or more of tag accelerometer data, orientation data, heading data, or tag movement data;
- transmitting and storing the one or more of the tag accelerometer data, the orientation data, the heading data, or the tag movement data to the datastore;
- determining positions of a plurality of location beacons in a coordinate system;
- transmitting and storing the positions of the plurality of location beacons to the datastore;
- processing, by the computer, the data stored in the datastore including the positions of the plurality of location beacons; and
- determining a location of the object based at least on the processed data.

15. The method of claim 14, further comprising:
- determining possible and impossible movement paths of the tag;
- transmitting the possible and impossible movement paths of the tag to the datastore;
- determining one or more of usage of logs or timestamps associated with the tag; and
- transmitting the one or more of the usage of logs or the timestamps associated with the tag to the datastore.

16. The method of claim 14, wherein the tag is a first tag, the method further comprising:
- determining received signal strength between a second tag and the one or more location beacons, wherein the second tag is associated with a person;
- transmitting and storing the received signal strength associated with the second tag to the datastore;
- determining one or more of tag accelerometer data, orientation data, heading data, or tag movement data associated with the second tag;
- transmitting and storing the one or more of the tag accelerometer data, the orientation data, the heading data, or the tag movement data associated with the second tag to the datastore;
- processing, by the computer, the data stored in the datastore; and
- determining a location of the person based at least on the processed data.

17. The method of claim 16, further comprising:
- determining possible and impossible movement paths of the second tag;
- transmitting and storing the possible and impossible movement paths of the second tag to the datastore;
- determining one or more of usage of logs or timestamps associated with the second tag; transmitting the one or more of the usage of logs or the timestamps associated with the second tag to the datastore;
- processing, by the computer, the data stored in the datastore; and
- determining the location of the person based at least on the processed data.

* * * * *